(12) United States Patent
Jing et al.

(10) Patent No.: US 11,788,060 B2
(45) Date of Patent: Oct. 17, 2023

(54) SMALL MOLECULE COMPOUND COMPOSITION THAT EFFICIENTLY INDUCES DIFFERENTIATION OF HUMAN PLURIPOTENT STEM CELLS INTO MYOCARDIAL CELLS

(71) Applicant: Shanghai Institute of Nutrition and Health, Chinese Academy of Sciences, Shanghai (CN)

(72) Inventors: Qing Jing, Shanghai (CN); Xiaoxu Qui, Shanghai (CN); Yang Liu, Shanghai (CN); Yifan Zhang, Shanghai (CN)

(73) Assignee: Shanghai Institutes for Biological Sciences Chinese Academy of Sciences, Shanghai (CN)

( * ) Notice: Subject to any disclaimer, the term of this patent is extended or adjusted under 35 U.S.C. 154(b) by 730 days.

(21) Appl. No.: 16/071,599

(22) PCT Filed: Jan. 12, 2017

(86) PCT No.: PCT/CN2017/070989
§ 371 (c)(1),
(2) Date: Jul. 20, 2018

(87) PCT Pub. No.: WO2017/124963
PCT Pub. Date: Jul. 27, 2017

(65) Prior Publication Data
US 2019/0032016 A1 Jan. 31, 2019

(30) Foreign Application Priority Data
Jan. 20, 2016 (CN) .................. 2016100381160.4

(51) Int. Cl.
C12N 5/077 (2010.01)
A61P 9/00 (2006.01)
C12N 5/0735 (2010.01)
C12N 5/0789 (2010.01)

(52) U.S. Cl.
CPC .............. C12N 5/0655 (2013.01); A61P 9/00 (2018.01); C12N 5/0606 (2013.01); C12N 5/0647 (2013.01); C12N 5/0657 (2013.01); C12N 2501/04 (2013.01); C12N 2501/415 (2013.01); C12N 2501/70 (2013.01); C12N 2506/45 (2013.01)

(58) Field of Classification Search
CPC .. C12N 5/0655; C12N 5/0657; C12N 5/0606; C12N 5/0647; C12N 2501/70; C12N 2501/04; C12N 2501/415; C12N 2506/45; A61P 9/00; B01J 27/24; B01J 35/004
See application file for complete search history.

(56) References Cited

U.S. PATENT DOCUMENTS

2014/0315943 A1 * 10/2014 Proia .................. A61P 35/00
514/293

FOREIGN PATENT DOCUMENTS

WO WO-2014062138 A1 * 4/2014 ........... C12N 5/0678

OTHER PUBLICATIONS

Liu et al. "Timely Inhibition of Notch Signaling by DAPT Promotes Cardiac Differentiation of Murine Pluripotent Stem Cells." PLOS One. 2014; 9(10): e109588. (Year: 2014).*
Mehta et al. "Phasic modulation of Wnt signaling enhances cardiac differentiation in human pluripotent stem cells by recapitulating developmental ontogeny"Biochim Biophys Acta.Nov. 2014;1843(11):2394-402 (Year: 2014).*
Murry and Keller. "Differentiation of Embryonic Stem Cells to Clinically Relevant Populations: Lessons from Embryonic Development."Cell.Feb. 22, 2008;132(4):661-80. (Year: 2008).*
Kadari et al. "Robust Generation of Cardiomyocytes from Human iPS Cells Requires Precise Modulation of BMP and WNT Signaling". Stem Cell Reviews and Reports vol. 11, pp. 560-569(2015) (Year: 2015).*
Kattmann et al. "Stage-Specific Optimization of Activin/Nodal and BMP Signaling Promotes Cardiac Differentiation of Mouse and Human Pluripotent Stem Cell Lines."Cell Stem Cell.Feb. 4, 2011;8(2):228-40. (Year: 2011).*
Jha et al. "Efficient Differentiation of Cardiomyocytes from Human Pluripotent Stem Cells with Growth Factors." Methods Mol Biol. 2015; 1299: 115-131. (Year: 2016).*
Batalov et al. "Differentiation of Cardiomyocytes from Human Pluripotent Stem Cells Using Monolayer Culture." Biomark Insights. 2015; 10(Suppl 1): 71-76. (Year: 2015).*
"Compound: LADUVIGLUSIB." https://www.ebi.ac.uk/chembl/compound_report_card/CHEMBL412142/. EMBL-EBI homepage. Website acessed Oct. 17, 2022. (Year: 2022).*
Varin et al. "Dual mTORC1/2 inhibition induces anti-proliferative effect in NF1-associated plexiform neurofibroma and malignant peripheral nerve sheath tumor cells." Oncotarget. 2016; 7:35753-35767 (Year: 2016).*

* cited by examiner

Primary Examiner — Titilayo Moloye
(74) Attorney, Agent, or Firm — Adam Bell; Matthew Raser (57) ABSTRACT

Disclosed is a small molecule compound composition that efficiently induces the differentiation of human pluripotent stem cells into myocardial cells. In particular, provided in the present invention is a small molecule compound composition. The small molecule compound composition comprises the following components: (i) an mTOR signaling pathway inhibitor; (ii) a Wnt pathway promoter; and (iii) optionally, a pharmaceutically acceptable carrier. The small molecule compound composition in the present invention can efficiently induce the differentiation of human pluripotent stem cells into myocardial cells. The preliminarily screened cardiomyocyte differentiation rate reaches up to 86%, and the optimized cardiomyocyte differentiation rate reaches up to 98.3%.

6 Claims, 5 Drawing Sheets

Figure 5

SMALL MOLECULE COMPOUND COMPOSITION THAT EFFICIENTLY INDUCES DIFFERENTIATION OF HUMAN PLURIPOTENT STEM CELLS INTO MYOCARDIAL CELLS

FIELD OF TECHNOLOGY

The invention relates to the field of biotechnology, in particular to a composition of small molecule compounds that efficiently induces differentiation of human pluripotent stem cells into myocardial cells.

BACKGROUND TECHNOLOGY

Cardiomyopathy is one of the major diseases in modern society that have the greatest morbidity and lethality, the myocardial damage caused by diseases such as myocardial ischemia and the like is irreversible cell death which still lacks effective treatment method until now. Since the discovery of human embryonic stem cell (hESC) and human induced pluripotent stem cell (hiPSC) (collectively referred to as human pluripotent stem cell (hPSC)), cardiomyocytes derived from hPSCs become a new hope in the field of cardiomyopathy treatment. Apart from cell-based therapy, cardiomyocytes derived from stem cells can also be used for therapeutic drug screening of cardiomyopathy, cardiac specific toxicity testing of drugs and other important aspects. In the past two decades, the field of human pluripotent stem cell directional differentiation and the application have made great development by leaps and bounds. In earlier times, the main method to gain cardiomyocytes is to co-culture human embryonic stem cells with mouse visceral endoderm-like cell (END-2), or by means of embryonic body (EB). These induction methods not only depend on serum of animal origin, but also have very low differentiation efficiency and output. In 2007, Charles Murry's lab established the monolayer cell differentiation system, by means of addition of cardiomyocyte differentiation-promoting cytokines, such as activin A and BMP4 in basic medium composed of RPMI1640 and B27, they have gained a differentiation efficiency of 30% with a human embryonic stem cell line H7, but an unsatisfactory efficiency of less than 5% with a human embryonic stem cell line H9. Later, it was optimized by adding Wnt3a in early stage of differentiation and then adding DKK1 to modulate the activity of Wnt signaling pathway (firstly activation and afterwards inhibition), so that there is a certain increase in differentiation efficiency, especially 30% of differentiation efficiency has also been obtained in H9 hESCs.

Although cardiac differentiation methods from the human embryonic stem cell have gained great progress after years of development, the differentiation efficiency still have elevating room, the differentiation stability and consistency between different cell lines also need a further promotion, more importantly, the factors which influence large scale production like differentiation cost and yield still need further improvement.

Therefore, there is an urgent need in the art to develop a small molecule compound and a method thereof that can greatly increase cardiomyocyte differentiation rate.

SUMMARY OF THE INVENTION

The object of the present invention is to provide a small molecule compound and a method thereof which can greatly increase the differentiation rate of cardiomyocytes.

In the first aspect of the present invention, a small molecular compound composition is provided, which comprises the following components:
(i) an mTOR signaling pathway inhibitor;
(ii) a Wnt pathway promoter; and
(iii) an optional, pharmaceutically acceptable carrier.

In another preferred embodiment, the small molecule compound composition comprises the following components:
(i) an mTOR signaling pathway inhibitor; and
(ii) a Wnt pathway promoter.

In another preferred embodiment, the molar ratio of the component (i) to the component (ii) is 1-5000: 5000-15000; preferably 2-500: 10000-12000; preferably 5-100: 10000-12000; most preferably 8-60: 10000-12000.

In another preferred embodiment, the working concentration of the composition comprises:
the working concentration of component (ii), Wnt pathway promoter is 1-40 µM, preferably 5-25 µM, more preferably 10-20 µM.

In another preferred embodiment, the working concentration of the composition comprises:
the working concentration of the component (i), mTOR signaling pathway inhibitor is 1-200 nM, preferably 5-100 nM, more preferably, 10-50 nM.

In another preferred embodiment, the mTOR signaling pathway inhibitor is selected from the group consisting of: rapamycin, everolimus (RAD001), KU-0063794, AZD8055, temsirolimus, INK128, ridaforolimus, and a combination thereof.

In another preferred embodiment, the Wnt pathway promoter comprises: CHIR99021, BIO, and a combination thereof.

In another preferred embodiment, the small molecule compound composition further comprises other cardiomyocyte differentiation promoter.

In another preferred embodiment, the other cardiomyocyte differentiation promoter comprises an AKT signaling pathway inhibitor LY99021.

In another preferred embodiment, the small molecule compound composition is a liquid composition, and the effective concentrations of the components are shown as follows:
mTOR signaling pathway inhibitor: rapamycin: 1 nM-0.2 µM, preferably 5 nM-0.1 µM, more preferably 10 nM-50 nM; everolimus (RAD001): 1 nM-0.2 µM, preferably, 5 nM-0.1 µM, more preferably 10 nM-50 nM; KU-0063794: 1 nM-0.2 µM, preferably 5 nM-0.1 µM, more preferably 10 nM-50 nM; AZD8055: 1 nM-0.2 µM, preferably, 5 nM-0.1 µM, more preferably, 10 nM-50 nM;
Wnt pathway promoter: CHIR99021: 1 µM-12 µM, preferably, 3µ-12 µM, more preferably, 10 µM-12 µM; Bio: 0.5 µM-2 µM, more preferably 1 µM-2 µM.

In the second aspect of the present invention, a use of a small molecule compound composition is provided for (i) promoting the differentiation of a stem cell into a cardiomyocyte.

In another preferred embodiment, the small molecule compound composition can further be used to (ii) increase the level of proliferation of a stem cell; and/or (iii) inhibit the stem cell apoptosis.

In another preferred embodiment, the level of proliferation comprises the number of proliferation of the stem cell and the activity of the stem cell.

In another preferred embodiment, the stem cell is selected from the group consisting of: a human induced pluripotent stem cell, an embryonic stem cell, and a combination thereof.

In another preferred embodiment, a totipotent stem cell is not included in the stem cell.

In another preferred embodiment, the stem cell is derived from a mammal, preferably a human, a rodent (such as mouse, rat).

In another preferred embodiment, the stem cell comprises a human induced pluripotent stem cell (hiPSC).

In another preferred embodiment, the human pluripotent stem cell is derived from: a skin fibroblast, a urine cell, a peripheral blood cell, and a combination thereof.

In the third aspect of the present invention, an in vitro method for inducing the differentiation of a stem cell into a cardiomyocyte is provided, which comprises:
  (a) in the presence of a combination of a differentiation-inducing compound, cultivating a stem cell line in a culture system, thereby obtaining the cardiomyocyte, wherein the combination of the differentiation-inducing compound comprises (i) an mTOR signaling pathway inhibitor; and (ii) a Wnt pathway promoter.

In another preferred embodiment, the molar ratio of the component (i) to the component (ii) in the culture system is 1-5000: 5000-15000; preferably 2-500: 10000-12000; preferably 5-100: 10000-12000; most preferably 8-60: 10000-12000.

In another preferred embodiment, the stem cell line comprises a pluripotent stem cell line or a multipotent stem cell.

In another preferred embodiment, the pluripotent stem cell line comprises a human pluripotent stem cell line.

In another preferred embodiment, the stem cell line is selected from the group consisting of: a human embryonic stem cell line H9-cTnT-eGFP, H9, H7, a human pluripotent stem cell line U-Q1, and a combination thereof.

In another preferred embodiment, the "cultivating" means cultivating the stem cell line for at least 10 passages, preferably at least 20 passages, more preferably at least 30-40 passages.

In another preferred embodiment, the combination of the differentiation-inducing compound is added during the initial stage of mesoderm formation (about −3 days) and maintained.

In another preferred embodiment, the "addition" comprises that (i) the mTOR signaling pathway inhibitor; and (ii) the Wnt pathway promoter are sequentially and simultaneously added.

In another preferred embodiment, the "addition" comprises the addition of (ii) the Wnt pathway promoter followed by (i) the mTOR signaling pathway inhibitor.

In another preferred embodiment, the "addition" renders the concentration of (i) the mTOR signaling pathway inhibitor is 1-200 nM, preferably 5-100 nM, more preferably 10-50 nM; and/or (ii) the concentration of the Wnt pathway promoter is 1-40 µM, preferably 5-25 µM, more preferably 10-20 µM in the culture system.

In another preferred embodiment, the method has one or more characteristics selected from the group consisting of:
  (i) a high cardiomyocyte differentiation rate which is 85-99.9%, preferably 90-98.5%; and
  (ii) during the cultivation process, $10^5$ stem cells are inoculated into 0.5 ml of the culture medium to produce $24\times10^5$ cardiomyocytes;

In another preferred embodiment, the method further comprises: (b) enriching and purifying the cardiomyocytes obtained in the step (a).

In another preferred embodiment, the purification condition comprises:
  (a1) purifying the culture medium: the culture medium is a basal medium supplemented with a 2-15% (w/w) of fetal bovine serum, in which the carbon source is substantially or completely composed of a lactose;
  (a2) cultivation time: 5-8 days, preferably 7-8 days.

In another preferred embodiment, the culture medium is a DMEM/F12 medium containing 0.1 mM-10 mM of lactose (preferably, 0.5 mM-5 mM, more preferably, 1 mM-4 mM) and supplemented with 2-15% (w/w) of fetal bovine serum.

In another preferred embodiment, a glucose is not contained in the culture medium (i.e., the glucose content is ≤0.05% by weight, based on the total weight of the culture medium).

In another preferred embodiment, the cardiomyocytes obtained after purification have a purity of 99.9%.

In another preferred embodiment, the method comprises both therapeutic and non-therapeutic method.

In another preferred embodiment, the density of the stem cell line in the culture system is $0.1\text{-}10\times10^5$ cells/ml, preferably $0.5\text{-}2\times10^5$ cells/ml.

In another preferred embodiment, the culture system is in a volume of from 0.1 to 1000 ml, preferably from 0.2 to 100 ml, more preferably from 0.3 to 10 ml, most preferably from 0.4 to 0.6 ml.

In another preferred embodiment, the ratio of the number of cardiomyocytes obtained M2 to the number of stem cells M1 (M2/M1) is 8-36, preferably 12-30, more preferably 16-28.

In the fourth aspect of the present invention, a cardiomyocyte is provided, which is prepared by the method according to the third aspect of the present invention.

In another preferred embodiment, the cardiomyocyte has one or more characteristics selected from the group consisting of:
  (i) high expression of a cardiomyocyte-specific structural gene; and
  (ii) high expression of an ion channel gene.

In the fifth aspect of the present invention, a kit for promoting the differentiation of a cardiomyocyte is provided, which comprises the small molecule compound composition of the first aspect of the present invention.

In another preferred embodiment, the kit further comprises other cardiomyocyte differentiation promoter.

In another preferred embodiment, the other cardiomyocyte differentiation promoter is selected from the group consisting of: a P38 MAPK signaling pathway inhibitor SB203580, ascorbic acid, retinoid acid, an AKT signaling pathway inhibitor LY99021, and a combination thereof.

In the sixth aspect of the present invention, a use of the cardiomyocyte according to the fourth aspect of the present invention is provided for the preparation of a pharmaceutical composition for preventing and/or treating a heart disease.

In another preferred embodiment, the heart disease comprises: ischemic heart failure, myocardial infarction, and a combination thereof.

In the seventh aspect of the present invention, a composition is provided, which comprises the cardiomyocyte according to the fourth aspect of the present invention.

In another preferred embodiment, the composition comprises a pharmaceutical composition, a food composition, a health care product composition.

In the eighth aspect of the present invention, a method of treating a heart disease is provided, comprising administering a safe and effective amount of the cardiomyocyte according to the fourth aspect of the present invention, and/or the composition according to the seventh aspect of the present invention to a subject in need thereof.

In another preferred embodiment, the administering comprises a topical injection administration.

In another preferred embodiment, the subject comprises a human or a non-human mammal.

In another preferred embodiment, the non-human mammal comprises a rodent such as a mouse or a rat.

It should be understood that, within the scope of the present invention, each technical feature of the present invention described above and in the following (as examples) may be combined with each other to form a new or preferred technical solution, which is not listed here due to space limitations.

DESCRIPTION OF FIGURE

Wherein, (A) shows the influence of rapamycin alone, CHIR alone and combination of rapamycin and CHIR on the differentiation rate of cardiomyocytes. In particular, a human embryonic stem cell line with myocardial specific fluorescent reporter gene is used under the condition of monolayer induction without cytokines. The screening results have showed that adding rapamycin (Rapa) during myocardial differentiation can significantly promote the differentiation rate of cardiomyocytes (left graph shows the ratio of GFP-expressing cells identified by fluorescence observation and right graph shows the ratio of GFP-positive cells identified by flow cytometry analysis, n=8, P<0.01, scale bars, 200 μm). (B) Detection of the specific working time window by adding and withdrawing rapamycin at the indicated time point (n=4,  P<0.01). (C) Prolonged treatment time of rapamycin can influence the yield of cardiomyocytes derived from stem cells (n=3,  P<0.01). (D) To test the promoting cardiac differentiation effect of rapamycin and the general adaptability of this small molecule induction method among different human pluripotent stem cell lines, using the same culture methods and conditions, the previous differentiation was repeated on the other 3 human pluripotent stem cells (human embryonic stem cells H7, H9 and human induced pluripotent stem cells U-Q1) and the efficiency of myocardial differentiation was determined by using flow cytometry to detect the proportion of cardiac troponin T (cTnT) positive cells (n=7, P<0.01). (E) Detailed schematic diagram of the differentiation method.

Wherein (A) indicates that flow cytometry analysis of cTnT-eGFP shows the purity of cardiomyocytes exceeds 99.9% after the differentiated cardiomyocytes are cultured in medium using lactate as the only carbon source for 7 days, the results are obtained from 4 independent repeated experiments. (B) α-actinin and cTnT immunofluorescence assay shows that the differentiated cardiomyocytes have a typical sarcomere structure (scale bars, 10 μm). (C) Transmission electron microscopy shows that the differentiated cardiomyocytes have normal myofibrils, sarcomere, intercalated disks and mature mitochondrial structure (MF, Z-band, ID and Mt, scale bars, 0.5 μm). (D) Cardiomyocytes obtained by rapamycin-induced monolayer differentiation have similar function and structural gene expressions (n=3) with those of classical EB-differentiated cardiomyocytes and normal human mature cardiomyocytes.

In this figure, human embryonic stem cells were seeded in 24 well culture plate with a density of $5 \times 10^4/cm^2$, and stimulated with different small molecules, cell number and cell viability were detected (CCK-8 cell viability detection method) every other day to record the influence of different small molecule compounds on cell number and cell viability of the stem cells.

Wherein figure (A and B) show the influence of different small molecules on proliferation rate of the stem cells by means of cell cycle analysis and BrdU proliferation detection. (C) Western blot analysis of intracellular Parp protein cleavage to estimate cell death under different treatment. (D) Influence of rapamycin on activity of apoptosis executive caspase 3/7 determined by luciferase reporter system. (E) Detection of the proportion of cell death treated with or without rapamycin by Annexin V/PI staining at the end of the culture on day 3 and day 4. (F) Whether or not apoptosis can be fully inhibited by addition of caspase inhibitor z-VAD-FMK is detected. All the results are statistically analyzed for at least 3 independently repeated experiments (* P<0.05, ** P<0.01).

Wherein cTnT+% indicates the differentiation rate of positive cardiomyocytes in all the above figures.

DETAILED DESCRIPTION

After extensive and in-depth research, the inventors have unexpectedly discovered that a combination of specific small molecule compounds can efficiently induce the transdifferentiation of pluripotent stem cells into cardiomyocytes through a large number of compound screenings. The preliminarily screened cardiomyocyte differentiation rate reaches 86%, the optimized cardiomyocyte differentiation rate is as high as 98.3%, and the cardiomyocytes after lactose enrichment and purification have a purity of as high as 99.9%.

Experiments have shown that when mTOR signaling pathway inhibitor and Wnt pathway promoter are used in combination on pluripotent stem cells (eg, human pluripotent stem cells), the pluripotent stem cell transdifferentiated cardiomyocytes have higher maturation and possess the structural basis to exert normal myocardial function, namely, have similar expression levels of myocardial specific structural genes and ion channel genes. In addition, the method for promoting cardiac differentiation in the present invention can also save half of the culture medium and additives, which greatly reduces the cost. On this basis, the inventors have completed the present invention.

mTOR Signaling Pathway Inhibitor mTOR is a serine-threonine protease, which is divided into two complexes, mTORC1 and mTORC2, depending on the different regulatory components. mTORC1 regulates the synthesis rate of intracellular protein mainly through activation phosphorylation of ribosomal protein S6 kinase 1 (S6K1 or p70s6K1) and inhibitory phosphorylation of 4E-binding protein (4E-BP).

mTOR signaling pathway inhibitors generally include: rapamycin, everolimus (RAD001), KU-0063794, AZD8055, temsirolimus, INK128, ridaforolimus, and the like.

In the present invention, the present invention detects the effects of mTOR signaling pathway inhibitors like rapamycin, everolimus (RAD001), KU-0063794 (Garcia-Martinez J M et al., Biochem J. 2009, 421(1): 29-42), AZD8055 (Chresta C M, et al. Cancer Res, 2010, 70(1), 288-298.) and the like on cardiomyocytes differentiation.

Wnt Pathway Promoter

The Wnt signaling pathway is the most important signaling pathway known to regulate cardiac development. Wnt proteins, such as Wnt3, are secreted glycoproteins that bind to receptors located on the cell membrane by paracrine or autocrine and activate intracellular signaling transduction molecules at all levels, mainly the entry of β-catenin into nucleus, to regulate target gene expression. Wnt pathway promoters usually include: CHIR99021 and BIO.

In the present invention, the present invention detects the effects of two Wnt pathway promoters including CHIR99021 (Bennett C N, et al. J Biol Chem, 2002, 277(34), 30998-31004.) and Bio (6-bromoindirubin-3'-oxime) on cardiomyocyte differentiation.

Small Molecule Compound Composition

As used herein, the term "small molecule compound composition" refers to a composition comprising the following components: (i) an mTOR signaling pathway inhibitor; and (ii) a Wnt pathway promoter. In addition, the small molecule compound composition may also contain a pharmaceutically acceptable carrier. In such a case, the small molecule compound composition is a pharmaceutical composition having the activity of inducing transdifferentiation of pluripotent stem cells into cardiomyocytes.

Among them, the mTOR signaling pathway inhibitors include: rapamycin, everolimus (RAD001), KU-0063794, AZD8055, temsirolimus, INK128, ridaforolimus.

The Wnt pathway promoters include: CHIR99021, BIO, and a combination thereof.

The ratio between the components that can be used in the small molecule composition of the present invention is not limited at all. In general, each component should meet its lowest effective concentration. In a preferred embodiment, the minimum effective concentration of each component in the small molecule compound composition is as follows:

mTOR signaling pathway inhibitor: rapamycin: 1 nM-0.2 µM, preferably, 1 nM-0.1 µM, more preferably, 10 nM-50 nM; everolimus (RAD001): 1 nM-0.2 µM, preferably, 1 nM-0.1 µM, more preferably, 10 nM-50 nM; KU-0063794: 1 nM-0.2 µM, preferably, 1 nM-0.1 µM, more preferably, 10 nM-50 nM; AZD8055: 1 nM-0.2 µM, Preferably, 1 nM-0.1 µM, more preferably 10 nM-50 nM;

Wnt pathway promoter: CHIR99021: 1 µM-12 µM, preferably, 3 µM-12 µM, more preferably, 10 µM-12 µM; Bio: 0.5 µM-2 µM, and more preferably, 1 µM-2 µM.

In the present invention, it was verified that the combination of rapamycin and CHIR99021 has good activity in inducing the differentiation of pluripotent stem cells into cardiomyocytes. Of course, those skilled in the art can also arbitrarily combine the above two types of inhibitors based on the enlightenment of the present invention to develop a novel small molecule compound composition having the activity to induce the transdifferentiation of pluripotent stem cells into cardiomyocytes.

As used herein, the terms "human pluripotent stem cells", "pluripotent stem cells", "hiPSC" are used interchangeably and all refer to isolated pluripotent stem cells derived from humans. In the present invention, the hiPSC of the present invention may be derived from human renal epithelial cells.

Cardiomyocyte

Cardiomyocytes have the basic characteristics of adult cardiomyocytes, including myofibers, sarcomere, intercellular connections (intercalated disc), mature mitochondria, and myocardial specific ion channels.

In the present invention, human pluripotent stem cells are induced to differentiate into cardiomyocytes by the small molecule compound composition (pharmaceutical composition) of the present invention, and the differentiated cardiomyocytes can be further differentiated into three subtypes: ventricular cardiomyocytes, atrial cardiomyocytes, and sinoatrial node cardiomyocytes.

Cardiomyocyte-Specific Structural Gene and Ion Channel Gene

As used herein, the terms "cardiomyocyte-specific structural gene" and "ion channel gene" refer to genes (or proteins thereof) that are highly expressed in cardiomyocytes compared to non-cardiomyocytes. In general, the cardiomyocyte-specific structural genes and ion channel genes include cTnT, αMHC, Nkx2.5, HCN4, Nav1.5, Cav3.2, and KCNQ1 etc.

Induction Method

The method for inducing the transdifferentiation of pluripotent stem cells (such as human pluripotent stem cells) into cardiomyocytes in the present invention generally refers to in vitro induction method. Of course, further in vivo induction may also be performed according to in vitro induction experiment, which may be studied and obtained according to conventional techniques or method in the art.

In general, the pluripotent stem cells can be cultured in the presence of the small molecule compound composition of the present invention.

In addition, the pluripotent stem cells (eg, human pluripotent stem cells) can be further cultured using a conventional cardiomyocyte medium in the art. Preferably, the cardiomyocyte culture medium may contain CHIR99021, an activator of the Wnt signaling pathway, rapamycin, an inhibitor of the mTOR signaling pathway, and a combination thereof.

In a preferred embodiment, the induction method of the present invention also includes the enrichment and purification of cardiomyocytes.

Pharmaceutical Composition

The present invention provides a composition comprising the cardiomyocytes of the present invention.

Preferably, the composition is a pharmaceutical composition, a food composition, a health care product composition, and the like.

The pharmaceutical composition of the present invention includes a pharmaceutically acceptable carrier and an effective amount of an active ingredient: the cardiomyocytes of the present invention.

As used herein, the term "effective amount" or "effective dose" refers to an amount that can be functional or active in humans and/or animals and acceptable to humans and/or animals.

As used herein, a "pharmaceutically acceptable carrier" component is a substance that is suitable for use in humans and/or mammals without undue adverse side effects (e.g., toxicity, irritation, and allergies), i.e., a substance having a reasonable benefit/risk ratio. The term "pharmaceutically acceptable carrier" refers to a carrier for the administration of a therapeutic agent, including various excipients and diluents.

The pharmaceutical composition of the present invention contains a safe and effective amount of the active ingredient of the present invention and a pharmaceutically acceptable carrier. Such carriers include, but are not limited to, saline, buffer, dextrose, water, glycerol, ethanol, and a combination thereof. In general, the pharmaceutical preparation should be matched with the administration method. The dosage form of the pharmaceutical composition of the present invention is an injection preparation, an oral preparation (tablet, capsule, oral liquid), a transdermal agent, and a sustained release agent. For example, it is prepared by a conventional method using physiological saline or an aqueous solution containing glucose and other adjuvants. The pharmaceutical compositions are preferably manufactured under aseptic conditions.

The effective amount of the active ingredient of the present invention may vary depending on the mode of administration and the severity of the disease to be treated. The choice of preferred effective amount can be determined by one of ordinary skilled in the art based on various factors (e.g., by clinical trials). Such factors include, but are not limited to: pharmacokinetic parameters of the active ingredient such as bioavailability, metabolism, half-life, etc.; severity of the disease of the patient to be treated, weight of the patient, immune status of the patient, administration routes and so on. In general, when the active ingredient of the present invention is administered at a dose of about 0.00001 mg-50 mg/kg animal body weight (preferably 0.0001 mg-10 mg/kg animal body weight) per day, a satisfactory effect can be obtained. For example, depending on the urgent need for treatment, several separate doses may be given daily or the dose may be proportionally reduced.

The pharmaceutically acceptable carriers described herein include, but are not limited to, water, saline, liposomes, lipids, proteins, protein-antibody conjugates, peptides, cellulose, nanogels, and a combination thereof. The choice of carrier should match the mode of administration and these are well known to those ordinary skilled in the art.

The present invention also provides a use of the pharmaceutical composition for preventing and/or treating heart disease.

The Main Advantages of the Present Invention Include:

(1) The method of the present invention can utilize a combination of inhibitors of specific signaling pathways to induce the transdifferentiation of pluripotent stem cells into cardiomyocytes. The differentiated cardiomyocytes have a higher maturity and possess the structural basis for exerting normal myocardial functions, that is, have similar expression levels of myocardial specific structural genes and ion channel genes.

(2) The method for promoting cardiac differentiation of the present invention can also save half of the culture medium and additives, which greatly reduces the cost.

(3) The method for promoting cardiac differentiation of the present invention has a higher cardiomyocyte differentiation rate, 1 stem cell can produce 24 cardiomyocytes, the preliminarily screened cardiomyocyte differentiation rate reaches 86%, and the optimized cardiomyocyte differentiation rate is as high as 98.3. % (H7 human embryonic stem cell line), the purity of cardiomyocytes obtained after enrichment and purification of cardiomyocytes is higher and can reach 99.9%.

Therefore, the present invention provides a better alternative strategy for related cell therapy.

The present invention is further described below with reference to specific embodiments. It should be understood that these examples are only for illustrating the present invention and not intended to limit the scope of the present invention. The conditions of the experimental methods not specifically indicated in the following examples are usually in accordance with conventional conditions as described in Sambrook et al., Molecular Cloning: A Laboratory Manual (New York: Cold Spring Harbor Laboratory Press, 1989) or the manufacturer's proposed conditions. Unless otherwise indicated, percentages and parts are by weight and parts by weight.

General Methods

The Culture of Human Pluripotent Stem Cell (hPSC)

Three hESC lines (H9-cTnT-eGFP, H9, H7) were available from WiCell stem cell bank (H9-hTnnTZ-pGZ-D2, WA09 and WA07). A human induced pluripotent stem cell line (hiPS-U-Q1) was established by using a DOX (Sigma-Aldrich)-induced OKSM four-factor lentivirus system to reprogram human urine cells (renal epithelial exfoliated cells) according to the reported method from Pei Duanqing's lab. All hPSCs were cultured on the trophoblast composed of CF1 mouse embryonic fibroblasts and the medium was a standard human embryonic stem cell culture medium which was DMEM/F12 medium supplemented with 20% Knock-Out serum replacer, 10 ng/mL human bFGF, 1 mM L-glutamine, 0.1 mM NEAA (all from Invitrogen) and 0.1 mM β-mercaptoethanol (Sigma-Aldrich). For the trophoblast-free culture, cloning of human pluripotent stem cells and growth of monolayers were maintained on human qualified Matrigel (BD Biosciences) in combination with mTeSR1 medium (STEMCELL Technologies).

Screening of Small Molecules that Promote the Differentiation of Stem Cells into Cardiomyocytes Based on the monolayer differentiation system established by Murry's laboratory, the present invention keeps the basic culture medium mTeSR1 and RPMI/B27 unchanged, and the time point of the liquid exchange and the addition of the induction factor unchanged, and then combines with the first promotion and post-inhibition function of the Wnt signaling pathway in myocardial differentiation, and uses CHIR99021 (Selleck) instead of Wnt3a. Activin A and BMP4, then replace DKK1 (PeproTech) with XAV939 (Enzo) and KY02111 (TOCRIS). A cardiac differentiation efficiency of about 10% was obtained with this primitive differentiation method in H9-cTnT-eGFP lines. Next, based on this method, screening for small molecule compounds that promote myocardial differentiation is performed. H9-cTnT-eGFP is inoculated in 48-well plates, and small-molecule candidates according to the appropriate concentration gradient are added from day 3 and withdrawn on day 12; on day 15, the differentiation efficiency is compared by observing the brightness of the green fluorescence in each well.

The small molecule compounds screened in this experiment are inhibitors or activators of the basic signaling pathways of stem cells and small molecules have been reported to be involved in stem cell differentiation, comprising LiCl, HN4Cl, Rapamycin, LY294002, Wortmannin, PD98059, PD0325901, SB431542, SB203580, SP600125, Retinoic acid, Asiatic acid, Y27632, Thiazovivin, z-VAD-FMK, VPA, TSA, VO-OHpic, SF1670, KU-55933, Resveratrol, STR1720, CX-4945, ABT-737, Nutlin-3, Pifithrin-α, Pifithrin-μ, GSK1904529A and FG-4592.

Method for Inducing the Differentiation of Human Pluripotent Stem Cells Monolayer into Cardiomyocytes Before differentiation, the cloning of the stem cells were cultured for at least 1 generation in feeder-free conditions, and digested to single cells by Accutase (Invitrogen) to cultivate for 1 generation in monolayer mode. Upon differentiation, hPSCs digested and dispersed into single cells were inoculated at a density of $5\times10^4/cm^2$ on Matrigel-precoated culture plates in human pluripotent stem cell culture medium (mTeSR1) for 2 days, followed by adding 12 µM CHIR and 10 nM rapamycin (Gene Operation company) to human pluripotent stem cell culture medium (mTeSR1) for another 3 days, the volume of culture medium was 0.5 mL for 24 well culture plates, 1 mL for 12 well culture plates, and so on, with medium replacement every day. Next, the medium was changed to RPMI/B27 minus insulin medium (Invitrogen) supplemented with 12 µM CHIR plus 10 nM rapamycin without insulin for 1 day, and then cells were cultured in RPMI/B27 medium supplemented with 10 µM XAV939 plus 10 µM KY02111 without insulin for continuous 4 days without medium replacement. Cells were continued to be cultivated in the insulin-free basic medium of RPMI/medium (Invitrogen) without the addition of any small molecules for 2 days, finally the culture was maintained in the basic medium of RPMI/B27 medium with insulin (Invitrogen) and the medium was changed once every 3 days. The model was indicated in FIG. 1E.

Cardiomyocyte Immunofluorescence

1. Antibody

Anti-cTnT, anti-α-actinin (CST) Antibody
Secondary antibodies of Alexa-488-anti-mouse, Alexa-555-anti-mouse (Invitrogen)

2. Experimental Procedure (1) Removing the complete medium and washing cells with PBS once;
(2) Fixing cells with 4% paraformaldehyde (Sigma-Aldrich) for 15 minutes at room temperature;
(3) Rinsing the cells with PBS three times at room temperature for 5 minutes each time;
(4) Permeabilizing the cells with PBS containing 0.1% Triton-X-100 (Sigma-Aldrich) for 15 minutes at room temperature;
(5) Rinsing the cells with PBS three times at room temperature for 10 minutes each time;
(6) Blocking the cells with PBS containing 5% goat serum (Invitrogen) at room temperature for 1 hour;
(7) Adding anti-cTnT, anti-a-actinin antibody 1:250, and the cells were incubated overnight at 4° C.;
(8) Rinsing the cells with PBS three times at room temperature for 10 minutes each time;
(9) Adding the corresponding fluorescent secondary antibody 1:1000 and the cells were incubated at room temperature in the dark for one hour;
(10) Removing the secondary antibody and rinsing the cells with PBS three times at room temperature for 10 minutes each time;
(11) Adding DAPI staining solution 1:2000 and the cells were incubated for 5 minutes at room temperature, rinsing the cells once with PBS at room temperature for 10 minutes each time;
(12) Sealing the specimen with a mounting medium and observing the result under a fluorescence microscope. The immunofluorescence photograph was taken with an Olympus fluorescence microscope.

Cardiomyocyte Electron Microscopy (1) Removing the culture solution, adding 1 ml of 2% glutaraldehyde, scraping the cells, and fixing it overnight at 4° C.;
(2) Fixing the cells with 0.25% Osmium/0.25% $K_4Fe(CN)6$ at 4° C. for 15-30 minutes;
(3) Rinsing the cells with PBS three times at 4° C. for 10 minutes each time;
(4) Dehydrating the cells with a series of acetone at room temperature.
50% acetone solution once, 10 minutes.
70% acetone solution once, 10 minutes.
90% acetone solution twice for 10 minutes each time.
100% acetone solution 3 times for 10 minutes each time.
(5) Soaking: removing the dehydrating agent in the bottle, adding 3 mL of pure acetone-EPON812 embedding agent (1:1 of volume ratio). After standing at room temperature for 30 minutes, discarding the diluted embedding agent and adding 1 mL of the pure embedding agent, and placing the bottle at room temperature for 2 hours or overnight.
(6) Embedding: dropping the mixed embedding agent on the bottom of the hole of the capsule module until it is full, moving the cell mass to the bottom of the capsule and closing it at both ends, putting it in an oven at 60° C. for 2 hours to cure it into a hard block;
(7) Repairing block: the embedded block was installed on a special fixture, the embedding agent on the surface was removed with a single-edged blade under the microscope;
(8) Slicing: The embedded block was first fixed on an ultramicrotome, and a half-thickness slice having a thickness of about 1 µm was cut and stained with hematoxylin-eosin staining Observing the cell image under the microscope, identifying the site where the ultrathin section is performed, and marking it. A φ3 mm, 150-200 mesh copper mesh was prepared, washed with a cleaning solution, and dehydrated and dried with anhydrous ethanol. Preparing a support membrane and carefully placing it on a copper grid. A triangular glass knife was mounted on the ultramicrotome, the embedded block was fixed, an ultrathin section having a thickness of 50 to 70 nm was cut out, the section was selected with a lash-pen, and taken out with a wire loop, attached to a side of the copper mesh having supporting membrane, and stored in dry dishes to be dyed;
(9) Electron staining: Using a clean petri dish and putting clean dental paraffin pieces inside it. Adding 1 to several drops of sodium acetate staining solution on the paraffin flakes, sandwiching the edges of the carrier with tweezers, and placing the sliced side down, so that the carrier floats on the droplets. The petri dish was covered and the cells were stained for 5 to 30 minutes. After dyeing, it was washed three times with double distilled water as soon as possible. Using filter paper to remove excess moisture from the carrier and setting the dishes to dry naturally. The carrier was placed in a separate petri dish, dyed with lead citrate and washed in the same manner. After the dyed sections were dried, they can be observed;
(10) Finally observing and taking photoes on a Leica FEI Tecnai G2 Spirit TEM transmission microscope.

Example 1 Screening of Small Molecule Compounds for Promoting Differentiation of Human Stem Cells into Cardiomyocytes Using H9-cTnT-eGFP human embryonic stem cell line as a reporter system, small molecule compounds capable of promoting efficient differentiation of stem cells into cardiomyocytes were screened under the condition of cytokine-free and high density monolayer culture.

After extensive screening, it was found that the combination of rapamycin, the inhibitor of mTOR signaling pathway, and CHIR99021, a promoter of Wnt pathway, can significantly promote the differentiation of human stem cells into cardiomyocytes.

Figure 1:
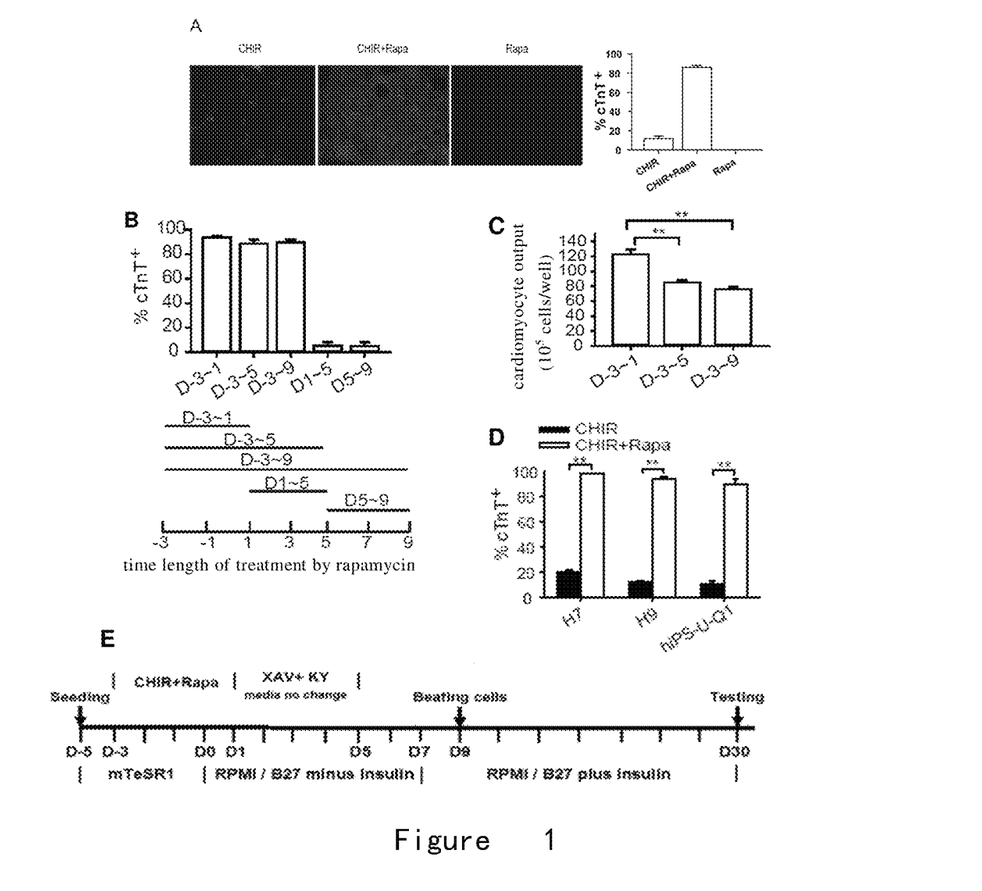
FIG. 1 shows that rapamycin promotes the differentiation of stem cells into cardiomyocytes.

Example 2 Combination of Rapamycin and CHIR99021 Promotes Differentiation of Human Stem Cells into Cardiomyocytes Primary Screening Results The result is shown in FIG. 1A. The results showed that the combination of mTOR signaling pathway inhibitor-Rapamycin and the Wnt pathway promoter CHIR99021 could significantly increase the efficiency of differentiation of human embryonic stem cells (H9 cell line) into cardiomyocytes, which reached 86%. However, the differentiation rate of cardiomyocytes obtained with CHIR99021 alone was very low, only about 15%, and the differentiation efficiency of cardiomyocytes obtained by using rapamycin alone was almost zero.

Optimized Results:

After treatment of human embryonic stem cells with CHIR (10 nM) and optimization of the time window for treatment with rapamycin (10 nM), the inventors added and withdrew rapamycin at the indicated time points. According to the characteristics of monolayer-based differentiation and the stage of cardiac differentiation, the entire differentiation process is divided into three stages, i.e., the formation stage of mesoderm from day −3 to day 1 (day 0 is defined as the initial time to induce differentiation, i.e., differentiation induction medium RPMI1640-B27 was used instead of pluripotent stem cell culture medium mTeSR1); the induction stage of cardiac precursor cells on days 1-5, and the emergence and expansion stage of cardiomyocytes after day 5. On the 30th day, the proportion of cardiomyocytes was determined by detecting H9-cTnT-eGFP differentiation. The inventors found that the addition of rapamycin at the initial stage of cardiac differentiation could produce 93.5±2.1% of cardiomyocytes (FIG. 1B), which was higher than that obtained by the addition of rapamycin throughout the whole process. At the same time, it was also found that prolonging the treatment time of rapamycin not only reduced the proportion of the final cardiomyocytes but also significantly reduced the yield of cardiomyocytes (FIG. 1C). If rapamycin was added only on days 1-5 or days 5-8, the proportion of cardiomyocytes produced was very low, and in many cases, the cells all died after day 5, resulting in the inability to obtain cardiomyocytes.

In order to examine the effect of combination of rapamycin and CHIR on promoting cardiac differentiation and the general applicability of this differentiation method between different human pluripotent stem cell lines, the inventors transplanted the optimized differentiation method as described above to three other human pluripotent stem cell lines (human embryonic stem cell line H9, H7 and human iPS stem cell line U-Q1) and tested the differentiation efficiency of cardiomyocytes in H9, H7, and U-Q1 cell lines.

As a result, it was found that the differentiation efficiency of the three stem cell lines was stable at a very high level. Among them, H7 cell line can achieve 98.3±0.76% differentiation efficiency in the above optimized differentiation system; the differentiation efficiency of human embryonic stem cell line H9 in the above-mentioned optimized differentiation system is 93.3±2.1%; and human iPS cells can also achieve a high differentiation efficiency of 90.6±3.6% in the above optimized differentiation system (FIG. 1D).

In addition, the differentiation method of the present invention can effectively save half of the culture medium and additive consumption, that is, the required culture medium per well of a 24 well plate is reduced from 1 ml to 0.5 ml per day (inoculation of 100 thousand stem cells per 0.5 ml of culture medium), meanwhile maintaining very high output efficiency of cardiomyocytes, one stem cell can produce 24 cardiomyocytes (counting on the fifteenth day of differentiation). $24 \times 10^5$ cardiomyocytes were produced per 0.5 ml of the culture medium. The final optimized differentiation method is shown in FIG. 1E.

Example 3 Enrichment and Purification of Cardiomyocytes Induced by Compounds

At day 15 of differentiation, the cardiomyocyte culture medium was changed to glucose-free DMEM/F12 medium containing 10% (v/v) fetal bovine serum (FBS). The medium was supplemented with 1 mM lactose as the sole carbon source, which was changed every two days and cultured continuously for 7 days. Flow cytometry analysis was used to detect the proportion of cTnT-positive cardiomyocytes.

Figure 2:
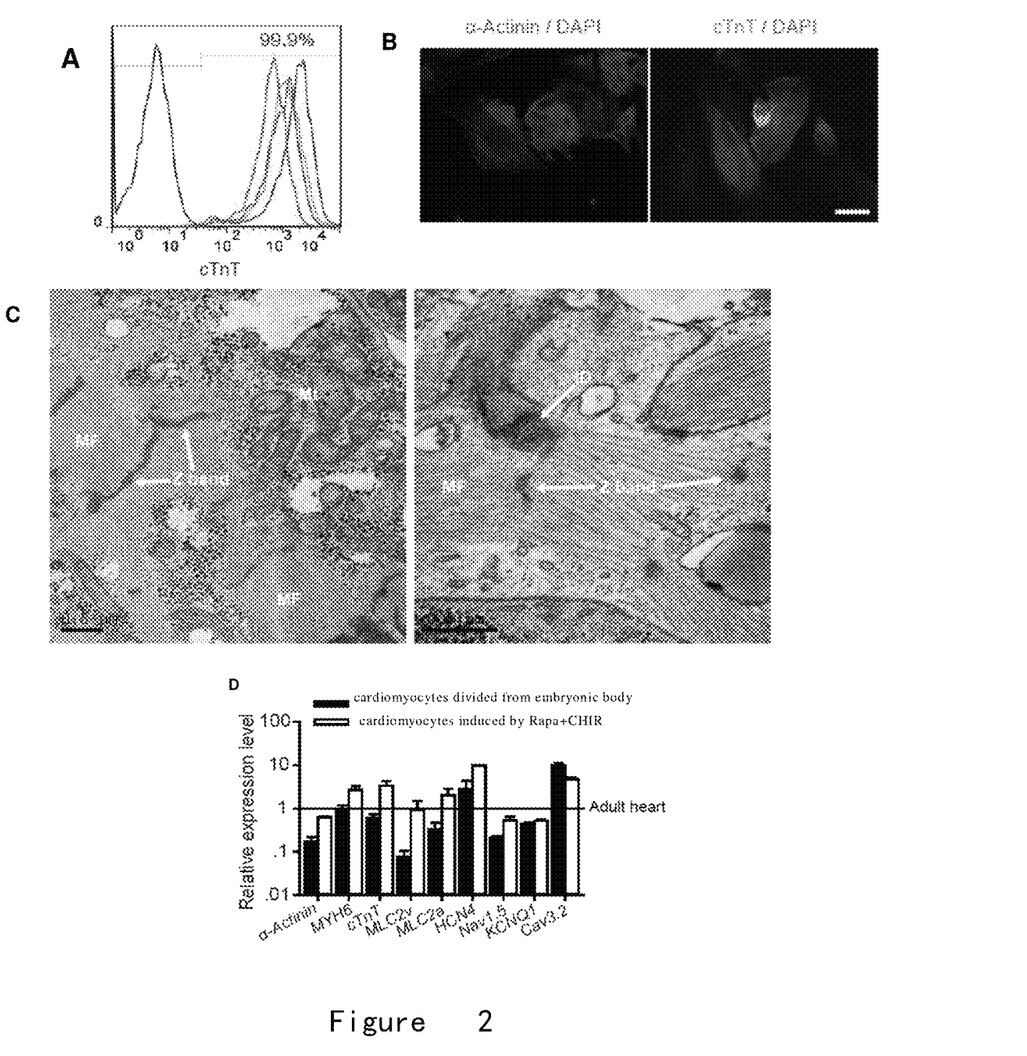
FIG. 2 shows cardiomyocytes induced and differentiated by rapamycin have signatures of mature cardiomyocytes.

The results showed that after stem cell-derived cardiomyocytes were cultured in 1 mM lactose (the only carbon source) culture medium for 7 days, the purity of cardiomyocytes reached to 99.9% (FIG. 2A). It was found that one stem cell input could produce 24 cardiomyocytes, and only need to consume half of the culture medium and additive factors.

Example 4 Identification of Specific Parameters of Cardiomyocytes Induced by Compounds By immunofluorescence staining, the present inventors found that differentiated cardiomyocytes expressed both proteins, some of which also have distinct sarcomere structure (FIG. 2B). The obtained cardiomyocytes have cardiomyocyte-like mature mitochondria (the stem cells have fewer mitochondria and most of them are spherical, and the mitochondrial inner membrane structure is not obvious); there are abundant myofilament structures, and the Z-line can be seen clearly; there are obvious cell junctions like intercalated disc (FIG. 2C).

The results indicated that the inducing method of the present invention produced cardiomyocytes with a higher degree of maturation and had a structural basis for exerting normal myocardial function.

In addition, cardiomyocyte-specific gene expression profiling revealed that cardiomyocytes differentiated by the method of the present invention had very similar expression levels of cardiac muscle specific structural genes such as cTnT, αMHC, Nkx2.5, HCN4, Nav1.5, Cav3.2, and KCNQ1 and ion channel genes to those obtained from the classical EB differentiation method and adult myocardium (FIG. 2D).

Example 5 Rapamycin Promotes the Growth of Human Embryonic Stem Cells Under Conditions of High Density Monolayer Culture by Inhibiting Apoptosis The differentiation of human embryonic stem cells into cardiomyocytes is a very complex and fragile process, and it is very sensitive to changes in various environmental factors and changes in cellular state. In particular, the monolayer based high-density differentiation method is more dependent on precise regulation than the EB differentiation method, and is also more dependent on the concentration level of autocrine cytokines. Any interference may result in a decrease in the differentiation efficiency or complete failure.

During the differentiation process, rapamycin-treated cells appeared morphologically more compact than CHIR treated cells and required longer time for enzyme digestion, and fewer dead cells floated during long-term culture. In order to confirm this phenomenon, the inventors examined the changes in cell number and cell activity during the culture.

The correlated detection was performed under three treatment conditions of DMSO, CHIR and CHIR+rapamycin. Cell counts showed that CHIR accelerated the increase in stem cell number in the first 3 days compared to DMSO solvent-treated control cells, while it reduced the sharp decrease of cell numbers on the 4th day. (Due to the replacement of the culture medium on the 4th day, stem cells underwent massive death because of the rapid changes in the environment). As a result, it was found that rapamycin can further increase the cell number and reduce the decrease in cell number (FIG. 3A).

Figure 3:
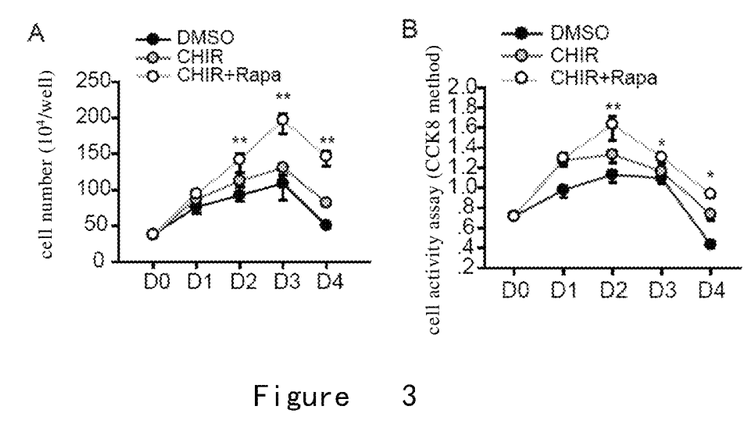
FIG. 3 shows that rapamycin promotes the increase in the number of human embryonic stem cells under high-density culture conditions.

Evaluation of cell proliferation levels and cell viability by measuring intracellular dehydrogenase activity using the CCK-8 kit also showed similar results, i.e., rapamycin can significantly increase cell number and activity (FIG. 3B).

Example 6 Influence of Rapamycin on Stem Cells 6.1 the Proliferation Rate of Stem Cells Under Treatment of Different Small Molecule Compositions by Cell Cycle Analysis and BrdU Cell Proliferation Assay BrdU Cell Proliferation Assay:

After 10 µM BrdU (Sigma-Aldrich) was added to incubate the cells for 1 hour, cells were harvested, digested and centrifuged at 300 g for 5 minutes. Cells were collected, washed once with PBS containing 0.5% BSA (wash solution) at room temperature, and resuspended in 1 ml of PBS. 3 ml of pre-cooled ethanol was added with shaking and settled for 20 minutes at room temperature. Centrifuge to remove the supernatant, wash once with PBS, centrifuge to remove supernatant, loosen the pellet by flicking a few times, add 1 ml of the freshly prepared denaturation solution (2M HCl) and mix. Allow to stand at room temperature for 20 minutes; add 1 ml of 0.1 M sodium borate (pH 8.5) to neutralize for 2 minutes at room temperature; rinse once and add anti-BrdU antibody (BD Biosciences 1:50 dilution) prepared with PBS containing 0.5% Tween 20/0.5% BSA (Sigma-Aldrich); aspirate primary antibody, rinse with 1 ml wash solution, add Alexa-488-anti-mouse (1:1000), incubate for 20 minutes at room temperature; aspirate secondary antibody, rinse again, resuspend with 0.5 ml 10 µg/ml PI solution and incubate for 30 minutes at room temperature. The supernatant was removed by centrifugation, rinsed again with a wash solution, and tested with flow cytometry.

Figure 4:
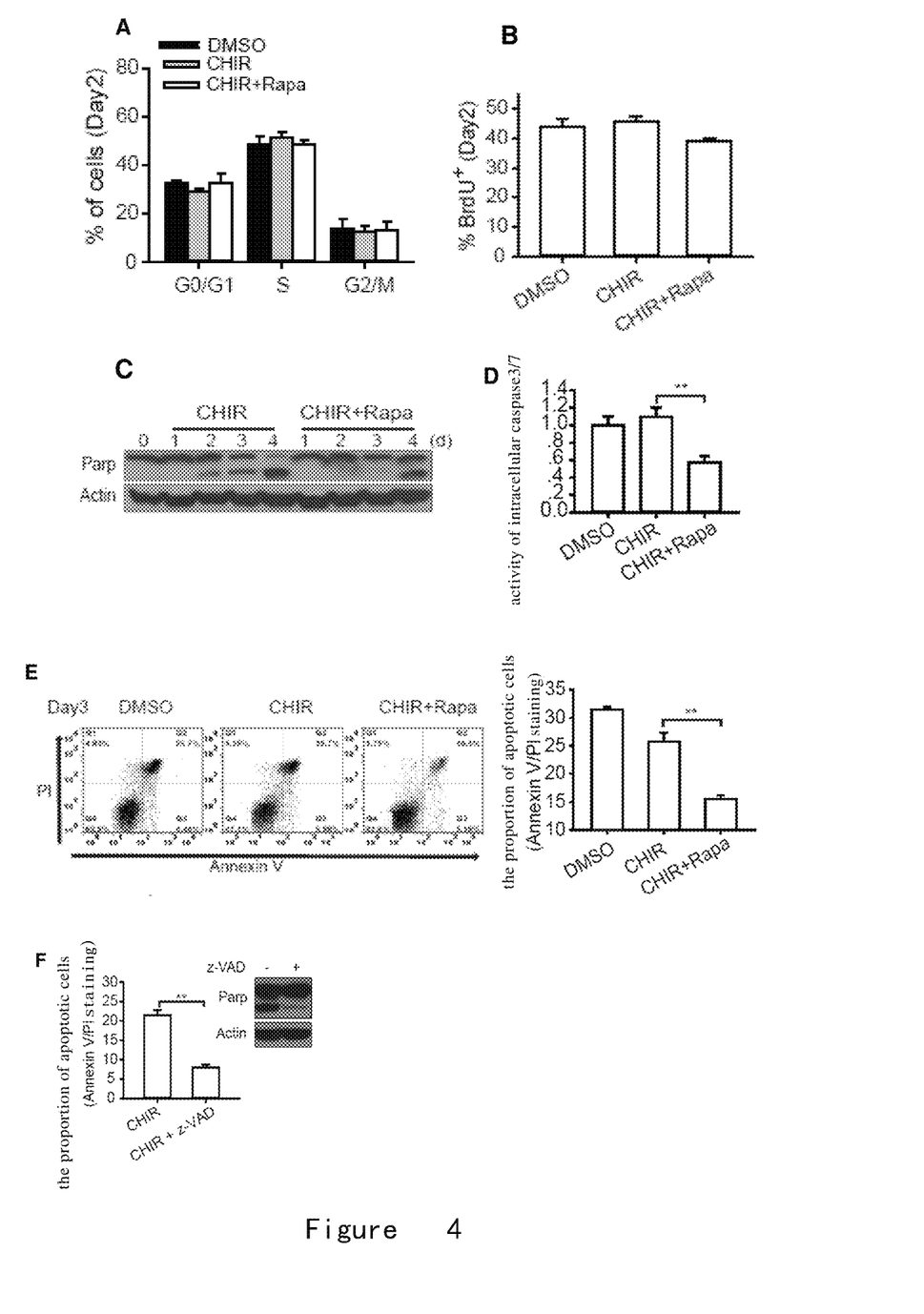
FIG. 4 shows that rapamycin inhibits stem cell apoptosis via mTOR.

The results showed that compared with the DMSO control group, CHIR slightly increased the proportion of cells in S phase and the proportion of BrdU positive cells, while rapamycin attenuated the promotion effect and the stem cell proliferation rate was similar to that of the DMSO group (FIGS. 4A, 4B). This is consistent with the classic concept that mTOR supports cell proliferation, while rapamycin inhibits cell proliferation.

6.2 Detecting the Effect of Rapamycin on Apoptosis

Caspase 3/7 Activity Assay: The Caspase-Glo 3/7 kit (Promega) was used for this experiment. The cells were seeded in a 96-well plate and treated with the corresponding small molecule for 2 days. After the pre-mixed reaction solution was added, the cells were fully lysed and incubated at 22° C. for 20 minutes. The fluorescence intensity was checked on the machine. For details, refer to the instruction manual.

Annexin V/PI staining: Annexin V/PI kit (Roche) was used in this experiment. The cells were cultured in 24-well plates. At the specified time, the cells were digested into single cells with accutase and washed once with PBS. The cells were incubated with staining solution containing Annexin V and PI for 10 minutes. Care was taken to avoid light. 5 volumes of incubation solution was added to dilute thereby stopping the reaction and tested by flow cytometry immediately, the excitation lights were 488 nm and 518 nm, the emission lights were 488-540 nm and 617 nm.

The cleavage of Parp, the most downstream marker protein of apoptosis, showed that the Parp cleavage band gradually increased with the increase of culture time during the first 4 days of CHIR treatment, reaching the highest value on the fourth day. However, rapamycin treatment significantly inhibited the cleavage of Parp, which was barely detectable in the first 3 days and only appeared on the 4th day (FIG. 4C). Caspase 3, 6, and 7 are the execution proteins of apoptosis and are mainly responsible for the cleavage of structural proteins and regulatory proteins in the nucleus and cytoplasm.

The caspase 3/7 luciferase reporter kit was used to detect the activity of endogenous caspase 3/7 in stem cells. The results showed that rapamycin treatment reduced the activity of intracellular caspase 3/7 to half of the level obtained by CHIR alone treatment (FIG. 4D).

Annexin V/PI double staining experiments showed that at the end of culture on the third day, the DMSO-treated group had an average of 31.4% Annexin V-positive apoptotic cells, while CHIR-treated group had 25.8% Annexin V-positive apoptotic cells, however, CHIR+ rapamycin treated group had only about 15.5% Annexin V-positive cells (FIG. 4E). On the 4th day, after replacing the RPMI/B27 differentiation medium for 24 hours, it was found that the group of cells that had previously only been supplemented with DMSO suffered severe death, and approximately 80% of the cells died. The CHIR treatment group also had nearly half of the deaths, and addition of rapamycin also significantly reduced the proportion of cell death (FIG. 4F).

The above results indicate that rapamycin can protect stem cells during differentiation and reduce the inhibition of apoptosis on efficient differentiation. This is also the reason that rapamycin can increase the production of cardiomyocytes.

Example 7 Combination of Other Compounds Induces Cardiomyocytes

The mTOR signaling pathway inhibitors Rapamycin analogue RAD001, KU0063794 and AZD8055 were combined with the Wnt pathway promoter CHIR, and the Wnt pathway promoter BIO was combined with Rapamycin or Rapamycin analogue RAD001 to observe the differentiation of cardiomyocytes.

The method was the same as the induced experimental scheme in Example 2. As a result, it was found that the compound combination of CHIR and RAD001, CHIR and KU0063794, CHIR and AZD8055 can generate cardiomyocytes under the same experimental conditions, and the cardiac differentiation rate was 78.8%, 68.75%, and 74.43%, respectively (FIG. 5a).

Figure 5:
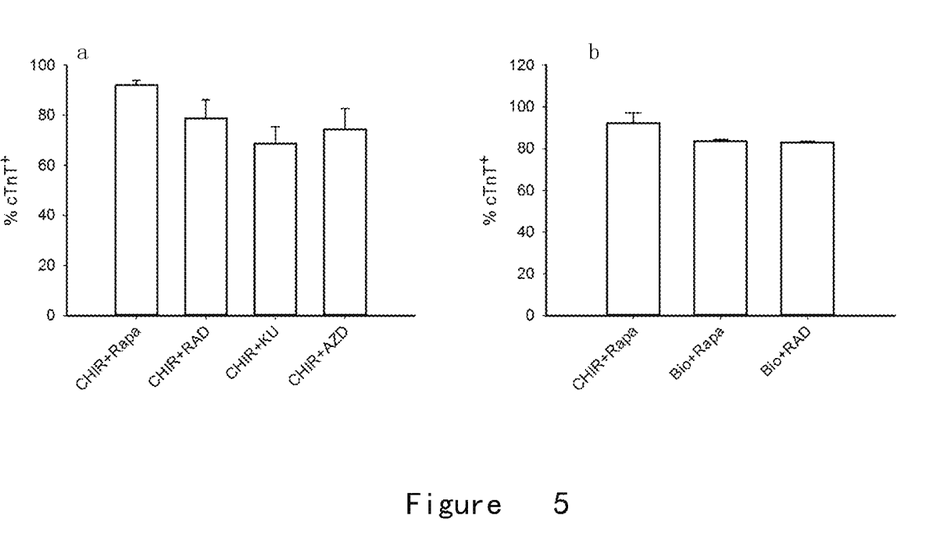
FIG. 5 shows the influence of other small molecule compositions on cardiomyocyte differentiation. Wherein (5a) shows the influence of analogues of rapamycin including RAD001, KU0063794 and AZD8055 combined with CHIR on myocardial differentiation efficiency; (5b) shows the influence of Wnt signaling activator BIO combined with rapamycin or its analogue on myocardial differentiation efficiency.

In addition, the compound combinations of BIO and Rapamycin, as well as BIO and RAD001 also produced cardiomyocytes with a cardiomyocyte differentiation rate of 83.47% and 82.9%, respectively (FIG. 5b).

These purified cardiomyocytes induced by compounds have the morphology of mature cardiomyocytes and have a structural basis for normal myocardial function.

Therefore, other mTOR signaling pathway inhibitor combined with Wnt signaling pathway promoter (such as CHIR and BIO) can also efficiently induce cardiomyocyte differentiation, and the differentiated cardiomyocytes have the characteristics of mature cardiomyocytes.

All publications mentioned herein are incorporated in the present application by reference as if each document is individually cited as a reference. It should also be understood that, after reading the above teachings of the present invention, those skilled in the art can make various changes or modifications, equivalents of which fall in the scope of claims as defined in the appended claims.

The invention claimed is:

1. A method for producing a cardiomyocyte, wherein said method comprises (1) culturing human pluripotent stem cells on plates coated with a solubilized basement membrane preparation extracted from the Engelbreth-Holm-Swarm (EHS) mouse sarcoma and in human pluripotent stem cell culture medium for 2 days, (2) after the 2 days, supplementing the medium of (1) with 12 µM CHIR plus 10 nM rapamycin and wherein the cells are cultured for 3 days, (3) after the 3 days, transferring and then culturing the cells of (2) in a medium comprising RPMI/B27 minus insulin supplemented with 12 µM CHIR plus 10 nM rapamycin without insulin for 1 day, and (4) after the 1 day, supplementing the medium of (3) with XAV939 plus 10 µM KY02111 for 4 days without medium replacement.

2. The method of claim 1, which further comprises: enriching and purifying the cardiomyocytes obtained.

3. The method of claim 1, which further comprises: mixing the cardiomyocyte with a pharmacologically acceptable carrier, thereby obtaining a cell preparation.

4. The method of claim 2, wherein the cardiomyocytes obtained after purification have a purity of 99.9%.

5. The method of claim 1, wherein the density of the human pluripotent stem cells in the human pluripotent stem cell culture medium is between $0.1 \times 10^5$ cells/ml and $10 \times 10^5$ cells/ml.

6. The method of claim 5, wherein the density of the human pluripotent stem cells in the human pluripotent stem cell culture medium is between $0.5 \times 10^5$ cells/ml and $2 \times 10^5$ cells/ml.

* * * * *